(12) United States Patent
Duvert

(10) Patent No.: US 6,565,892 B2
(45) Date of Patent: May 20, 2003

(54) SYNERGISTIC FUNGICIDAL COMPOSITION COMPRISING A COMPOUND ANALOGOUS TO STROBILURIN

(75) Inventor: Patrice Duvert, Lyons (FR)

(73) Assignee: Rhone-Poulenc Agrochimie, Lyons (FR)

( * ) Notice: Subject to any disclaimer, the term of this patent is extended or adjusted under 35 U.S.C. 154(b) by 0 days.

(21) Appl. No.: 09/897,457

(22) Filed: Jul. 3, 2001

(65) Prior Publication Data

US 2001/0046978 A1 Nov. 29, 2001

Related U.S. Application Data

(60) Continuation of application No. 09/634,871, filed on Aug. 7, 2000, now abandoned, which is a division of application No. 09/452,158, filed on Dec. 1, 1999, now Pat. No. 6,156,740, which is a division of application No. 08/983,625, filed as application No. PCT/FR96/01155 on Jul. 23, 1996, now Pat. No. 6,015,802.

(30) Foreign Application Priority Data

Jul. 24, 1995 (FR) ............................. 95 09183

(51) Int. Cl.$^7$ .................. A01N 57/12; A01N 57/02; A01N 59/26; A01N 37/50
(52) U.S. Cl. ................ 424/605; 424/601; 424/602; 424/604; 424/606; 514/141; 514/492; 514/506; 514/539
(58) Field of Search .................. 514/539, 141, 514/506, 492; 424/601, 602, 605, 606, 604

(56) References Cited

U.S. PATENT DOCUMENTS

| | | | |
|---|---|---|---|
| 4,829,085 A | 5/1989 | Wenderoth et al. | 514/522 |
| RE33,989 E | 7/1992 | Wenderoth et al. | 514/522 |

FOREIGN PATENT DOCUMENTS

| | | |
|---|---|---|
| EP | 0253213 | 1/1988 |
| EP | 0398692 | 11/1990 |
| EP | 0741970 | 11/1996 |
| WO | 92/08703 | 5/1992 |
| WO | 95/15083 | 6/1995 |

OTHER PUBLICATIONS

Research Disclosure, vol. 338, No. 33893, Jun. 1992, pp. 506–510, published by Industrial Opportunities, Havant, England.

Research Disclosure, vol. 348, No. 34874, Apr. 1993, pp. 267–268, published by Industrial Opportunities, Havant England.

Tammes, *Neth. J. Plant Path. 70* (1964), pp. 73–80, published by Nederlands planteziektenkundige vereniging, Wageningen, The Netherlands.

*The Pesticide Manual*, ed. Clive Tomlin, 10$^{th}$ edition, 1994, pp. 68, 530–532 and 579, published by the British Crop Protection Council, Farnham, Surrey, UK.

*Primary Examiner*—John Pak
(74) *Attorney, Agent, or Firm*—Burns, Doane, Swecker & Mathis, L.L.P.

(57) ABSTRACT

Synergistic fungicidal composition comprising a compound analogous to strobilurin of formula (I):

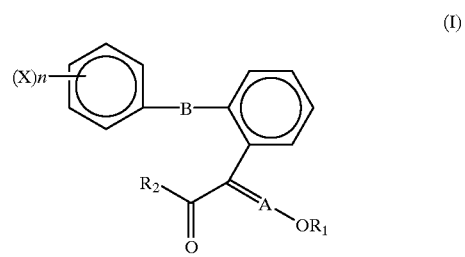

in which:

A is the nitrogen atom or the —CH group,

B is the —OCH$_2$— or —CH$_2$O— or CH(CH$_3$)—O—N═CH— or —CH═N—O—CH(CH$_3$)— group or the group

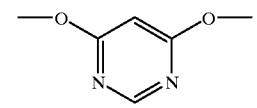

R$_1$ is an alkyl group containing 1 to 4 carbon atoms, R$_2$ is —OCH$_3$ or —NHCH$_3$, X is a halogen atom, the cyano group or an alkyl or haloalkyl group containing 1 to 4 carbon atoms, n is equal to 1 or 2, with, when n is equal to 2, the possibility of having different X groups, and at least one fungicidal compound B, and a process for the curative or preventive control of phytopathogenic fungi using the composition.

53 Claims, 1 Drawing Sheet

Dose of ICI A5504 (in ppm)

Dose of SSF-129 (in ppm)

SYNERGISTIC FUNGICIDAL COMPOSITION COMPRISING A COMPOUND ANALOGOUS TO STROBILURIN

CROSS-REFERENCE TO RELATED APPLICATIONS

This application is a continuation of application Ser. No. 09/634,871, filed Aug. 7, 2000, now abandoned, incorporated by reference herein in its entirety and relied upon, which is a divisional of application Ser. No. 09/452,158, filed Dec. 1, 1999, now U.S. Pat. No. 6,156,740, which is a divisional of application Ser. No. 08/983,625, filed May 13, 1998, now U.S. Pat. No. 6,015,802, incorporated by reference herein in its entirety and relied upon, which is a 371 of International Application No. PCT/FR96/01155, filed Jul. 23, 1996, and published by the International Bureau in French, not in English, on Feb. 6, 1997 as WO 97/03563.

BACKGROUND OF THE INVENTION

The subject of the present invention is a synergistic fungicidal composition comprising a compound analogous to strobilurin and a process which makes use of the said composition and which is intended for the curative or preventive protection of crops against fungal attacks.

Compounds analogous to strobilurin with a fungicidal effect are known, in particular from European Patent Application EP 253213 or 398692 or from international Application WO 92/08703, which make it possible to prevent the growth and the development of phytopathogenic fungi capable of attacking crops.

SUMMARY AND OBJECTS OF THE INVENTION

However, it is always desirable to improve the spectrum of activity and the effectiveness of such compounds with a fungicidal effect or to reinforce them by combining them with other molecules in order to obtain a more effective product (combination with a systemic fungicide, these fungicides instead being molecules of "contact" type) or alternatively to prevent the appearance of fungal strains which are resistant to these new fungicides.

It is also highly desirable to have available fungicidal products which enjoy an improved persistence of effect, likely to space out in time the number of plant-protection treatments necessary for satisfactory control of the parasites.

It is, in any event, particularly advantageous to be able to decrease the amount of chemicals distributed in the environment, while ensuring high-performance protection of crops against fungal attacks.

It has now been found that one (or a number) of the above objects could be achieved by virtue of the fungicidal composition according to the present invention.

The present invention accordingly provides a synergistic fungicidal composition comprising at least one compound A of formula (I):

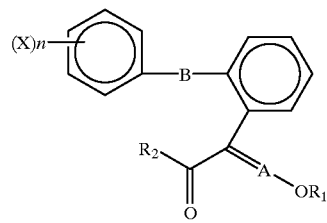

in which:

A is the nitrogen atom or the —CH group,

B is the —OCH$_2$— or —CH$_2$O— or —CH(CH$_3$)—O—N=CH— or —CH=N—O—CH(CH$_3$)— group or the group

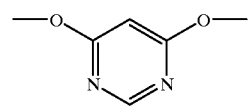

R$_1$ is an alkyl group containing 1 to 4 carbon atoms, preferably the methyl group, R$_2$ is —OCH$_3$ or —NHCH$_3$, X is a halogen atom, the cyano group or an alkyl or haloalkyl group containing 1 to 4 carbon atoms, preferably the methyl or trifluoromethyl group, n is equal to 1 or 2, with, when n is equal to 2, the possibility of having different X groups, and at least one fungicidal compound B chosen from the group consisting of phosphorous acid and derivatives thereof, for example metal phosphites, such as fosetyl-Al, and alkali metal or alkaline-earth metal salts of phosphorous acid. The compositions will generally contain one compound A.

DETAILED DESCRIPTION OF INVENTION

Figure 1:
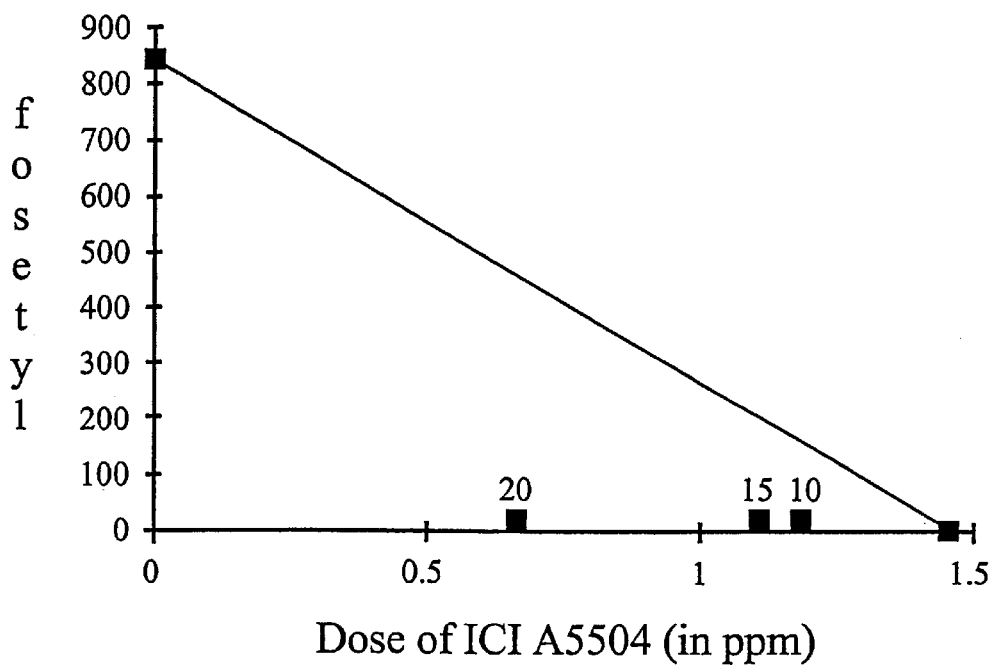
FIG. 1 is an isobole plot for ICIA 5504, i.e. methyl (E)-2-{2-[6-(2-cyanophenoxy)pyrimidin-4-yloxy]phenyl}-3-methoxyacrylate, and fosetyl-Al in Chardonnay vine cuttings against *Plasmopara viticola* (grape downey mildew)

The fungicidal composition according to the invention advantageously comprises the components A and B in an A/B ratio by weight of from 0.004 to 1, preferably from 0.0125 to 0.4.

It is clearly understood that the said fungicidal composition can contain a single compound B or more than one such compound, for example 1, 2 or 3 compounds B, according to the use for which the combination is intended. The composition may also comprise more than one compound A.

Preference is given to the fungicidal composition according to the invention in which the compound A is methyl (E)-2-{2-[6-(2-cyanophenoxy)pyrimidin-4-yloxy]phenyl}-3-methoxyacrylate, methyl (E)-methoxyimino[α-(o-tolyloxy)-o-tolyl]acetate or N-methyl-(E)-methoxyimino[2-(2,5-dimethylphenoxymethyl)phenyl]acetamide.

Preference is further given, among the more especially preferred meanings of the compound B defined above, to fosetyl-Al. In an entirely unexpected way, the combination according to the invention then significantly improves the effect of the active materials taken separately with respect to a number of fungi which are particularly harmful to crops, for example in particular grapes or the Solanaceae. This improvement is reflected in particular by a decrease in the doses of each of the constituents, which is particularly advantageous for the user and the environment. The fungicidal product thus exhibits synergistic properties attested by application of the Tammes method, "Isoboles, a graphic representation of synergism in pesticides", Netherlands Journal of Plant Pathology, 70(1964), p. 73–80.

Preferably, when the component B is fosetyl-Al, the A/B ratio is from 0.01 to 1, preferably from 0.033 to 0.4, for all the crops envisaged.

In the particular case of lawns, the A/B ratio will be from 0.004 to 0.4, or from 0.004 up to but not including 0.4, preferably from 0.0125 to 0.1.

The structures corresponding to the common names of the fungicidal active materials which appear in the definition of B are shown in at least one of the following 2 works:

"The Pesticide Manual", edited by Clive Tomlin and published by The British Crop Protection Council, $10^{th}$ edition;

1' Index phytosanitaire [Plant-protection index] 1994, published by 1' Association de Coordination Technique Agricole [Agricultural Technical Coordination Association], $30^{th}$ edition.

As regards the compounds A analogous to strobilurin, methyl (E)-2-{2 -[6-(2-cyanophenoxy)pyrimidin-4-yloxy] phenyl}-3-methoxyacrylate (or ICIA5504) is described in International Application WO 9208703; methyl (E)-methoxyimino[α-(o-tolyloxy)-o-tolyl]acetate (or BAS490F) is described in European Patent Application EP 253213; and N-methyl-(E)-methoxyimino[2-(2,5-dimethylphenoxymethyl)phenyl]acetamide (or SSF-129) is described in European Patent Application EP 398692. Moreover, ICIA5504 and BAS490F are listed in the above-mentioned work "The Pesticide Manual".

The fungicidal composition according to the invention comprises, as active material, at least one compound A and at least one compound B as a mixture with solid or liquid vehicles which are acceptable in agriculture and/or surface-active agents which are also acceptable in agriculture. In particular, the inert and conventional vehicles and the conventional surface-active agents can be used. These compositions cover not only compositions which are ready to be applied to the crop to be treated by means of a suitable device, such as a spray device, but also commercial concentrated compositions which have to be diluted before application to the crop. The combination of at least one compound A with at least one compound B is denoted as active material.

These compositions can also contain any kind of other ingredients such as, for example, protective colloids, adhesives, thickening agents, thixotropic agents, penetrating agents, stabilizing agents, sequestering agents and the like. More generally, the compounds A and B can be combined with all the solid or liquid additives corresponding to the conventional formulating techniques.

Generally, the compositions according to the invention usually contain from 0.05 to 95% (by weight) of active material, one or more solid or liquid vehicles and, optionally, one or more surface-active agents.

In the present account, the term "vehicle" denotes a natural or synthetic, organic or inorganic material with which the active material is combined to facilitate its application on the aerial parts of the plant. This vehicle is thus generally inert and it must be acceptable in agriculture, especially on the treated plant. The vehicle can be solid (clays, natural or synthetic silicates, silica, resins, waxes, solid fertilizers and the like) or liquid (water, alcohols, especially butanol, and the like).

The surface-active agent can be an emulsifying, dispersing or wetting agent of ionic or nonionic type or a mixture of such surface-active agents. There may be mentioned, for example, salts of polyacrylic acids, salts of lignosulphonic acids, salts of phenolsulphonic or naphthalenesulphonic acids, polycondensates of ethylene oxide with fatty alcohols or with fatty acids or with fatty amines, substituted phenols, (especially alkylphenols or arylphenols), salts of esters of sulphosuccinic acids, taurine derivatives (especially alkyltaurates), phosphoric esters of polyoxyethylenated phenols or alcohols, esters of fatty acids and of polyols, and the derivatives of the above compounds containing sulphate, sulphonate and phosphate functional groups. The presence of at least one surface-active agent is generally indispensable when the active material and/or the inert vehicle is/are not soluble in water and the carrier agent for application is water.

The compositions for agricultural use according to the invention can thus contain the active material within very wide limits, ranging from 0.05% to 95% (by weight). Their surface-active agent content is advantageously of between 5% and 40% by weight. Unless otherwise specified percentages in this specification, including the accompanying claims, are by weight.

These compositions according to the invention are themselves in fairly diverse, solid or liquid forms.

There may be mentioned, as forms of solid compositions, the powders for dusting (with an active material content which can range up to 100%) and the granules, especially those obtained by extrusion, by compacting, by impregnation of a granulated support, or by granulation from a powder (the active material content in these granules being between 0.5 and 80% for the latter cases), the tablets or effervescent tablets.

The fungicidal composition according to the invention can also be used in the form of powders for dusting; it in also possible to use a composition comprising 50 g of active material and 950 g of talc; it is also possible to use a composition comprising 20 g of active material, 10 g of finely divided silica and 970 g of talc; these constituents are mixed and milled and the mixture is applied by dusting.

There may be mentioned, as forms of liquid compositions or those intended to constitute liquid compositions at the time of application, solutions, in particular water-soluble concentrates, emulsions, suspension concentrates, aerosols, wettable powders (or powder to be sprayed), pastes or gels.

The suspension concentrates, which can be applied by spraying, are prepared so as to obtain a stable fluid product which does not settle out and they generally contain from 10 to 75% of active material, from 0.5 to 15% of surface-active agents, from 0.1 to 10% of thixotropic agents and from 0 to 10% of suitable additives, such as antifoaming agents, corrosion inhibitors, stabilizing agents, penetrating agents and adhesives and, as vehicle, water or an organic liquid in which the active material is insoluble or nearly insoluble: certain organic solid materials or inorganic salts can be dissolved in the vehicle to aid in preventing sedimentation or as antigels for water.

A suspension concentrate composition in given here as an example:

SC EXAMPLE 1

| | |
|---|---|
| active material | 500 g |
| polyethoxylated tristyrylphenyl phosphate | 50 g |
| polyethoxylated alkylphenol | 50 g |
| sodium polycarboxylate | 20 g |
| ethylene glycol | 50 g |
| organopolysiloxane oil (antifoaming agent) | 1 g |
| polysaccharide | 1.5 g |
| water | 316.5 g |

Wettable powders (or powder to be sprayed) are generally prepared so that they contain 20 to 95% of active material, and they generally contain, in addition to the solid vehicle, from 0 to 30% of a wetting agent, from 3 to 20% of a dispersing agent and, when this is necessary, from 0.1 to 10% of one or more stabilizing agents and/or other additives, such as penetrating agents, adhesives, or anticlumping agents, dyes, and the like.

To obtain powders to be sprayed or wettable powders, the active materials are intimately mixed, in suitable mixers, with the additional substances and the mixture is milled with mills or other suitable grinders. Powders to be sprayed are thereby obtained with advantageous wettability and suspensibility; they can be suspended in water at any desired concentration and these suspensions can be used very advantageously in particular for application to plant leaves.

Pastes can be produced in place of wettable powders. The conditions and modes of production and use of these pastes are similar to those of wettable powders or powders to be sprayed.

Various wettable powder (or powder to be sprayed) compositions are given here as examples:

WP EXAMPLE 1

| | |
|---|---|
| active material | 50% |
| ethoxylated fatty alcohol (wetting agent) | 2.5% |
| ethoxylated phenylethylphenol (dispersing agent) | 5% |
| chalk (inert vehicle) | 42.5% |

WP EXAMPLE 2

| | |
|---|---|
| active material | 10% |
| C13 branched-type synthetic oxo alcohol, ethoxylated with 8 to 10 molecules of ethylene oxide (wetting agent) | 0.75% |
| neutral calcium lignosulphonate (dispersing agent) | 12% |
| calcium carbonate (inert filler) | qs for 100% |

This wettable powder contains the same ingredients as in the above example, in the proportions below:

WP EXAMPLE 3

| | |
|---|---|
| active material | 75% |
| wetting agent | 1.50% |
| dispersing agent | 8% |
| calcium carbonate (inert filler) | qs for 100% |

WP EXAMPLE 4

| | |
|---|---|
| active material | 90% |
| ethoxylated fatty alcohol (wetting agent) | 4% |
| ethoxylated phenylethylphenol (dispersing agent) | 6% |

WP EXAMPLE 5

| | |
|---|---|
| active material | 50% |
| mixture of anionic and nonionic surface-active agents (wetting agent) | 2.5% |
| sodium lignosulphonate (dispersing agent) | 5% |
| kaolin clay (inert vehicle) | 42.5% |

Aqueous dispersions and emulsions, for example the compositions obtained by diluting a wettable powder or an emulsifiable concentrate according to the invention with water, are contained within the general scope of the present invention. Emulsions can be of the water-in-oil or oil-in-water type and they can have a thick consistency, like that of a "mayonnaise".

The fungicidal compositions according to the invention can be formulated in the form of water-dispersible granules, which also come within the scope of the invention.

These dispersible granules, with a bulk density generally of between approximately 0.3 and 0.6, have a particle size generally of between approximately 150 and 2000 and preferably between 300 and 1500 microns.

The active material content of these granules is generally between approximately 1% and 90%, and preferably between 25% and 90%.

The rest of the granule is essentially composed of a solid filler and, optionally, of surface-active adjuvants which confer water-dispersibility properties on the granule. These granules can be essentially of two distinct types according to whether the filler held is soluble or insoluble in water. When the filler is water-soluble, it can be inorganic or, preferably, organic. Excellent results were obtained with urea. In the case of an insoluble filler, the latter is preferably inorganic, such as, for example, kaolin or bentonite. It in then advantageously accompanied by surface-active agents (in a proportion of 2 to 20% by weight of the granule) of which more than half consists of, for example, at least one dispersing agent, essentially anionic, such as an alkali metal or alkaline-earth metal polynaphthalenesulphonate or an alkali metal or alkaline-earth metal lignosulphonate, the remainder consisting of nonionic or anionic wetting agents such as an alkali metal or alkaline-earth metal alkylnaphthalenesulphonate.

Moreover, although this is not indispensable, it in possible to add other adjuvants such an antifoaming agents.

The granule according to the invention can be prepared by mixing the necessary ingredients and then granulating according to several techniques known per se (granulator, fluid bed, sprayer, extrusion, and the like). The preparation generally finishes with a crushing followed by a sieving to the particle size chosen within the limits mentioned above. Granules obtained as above and then impregnated with a composition containing the active material can alternatively be used.

It is preferably obtained by extrusion, by carrying out the preparation as indicated in the examples below.

DG EXAMPLE 1

Dispersible Granules

90% by weight of active material and 10% of urea in the form of pearls are mixed in a mixer. The mixture is then milled in a pin mill. A powder is obtained which is moistened with approximately 8% by weight of water. The moist powder is extruded in a perforated-roller extruder. A granular material in obtained which in dried, and then crushed and sieved, so as to respectively keep only the granules with a size of between 150 and 2000 microns.

DG EXAMPLE 2

Dispersible Granules

The following constituents are mixed in a mixer:

| | |
|---|---|
| active material | 75% |
| wetting agent (sodium alkylnaphthalene-sulphonate | 2% |
| dispersing agent (sodium polynaphthalene-sulphonate) | 8% |
| water-insoluble inert filler (kaolin) | 15% |

This mixture is granulated on a fluid bed in the presence of water and then dried, crushed and sieved so as to obtain granules with a size of between 0.15 and 0.80 mm.

These granules can be used alone or in solution or dispersion in water so as to obtain the required dose. They can also be used to prepare combinations with other active materials, especially fungicides, the latter being in the form of wettable powders or granules or aqueous suspensions.

As regards the compositions which are suitable for storage and transportation, they more advantageously contain from 0.5 to 95% (by weight) of active material.

A further feature of the invention in a process for the curative or preventive control of fungi which are phytopathogenic, for example towards crops or lawns, characterized in that an effective and non-phytotoxic amount, in combination, of at least one compound A and at least one compound B, for example in a fungicidal composition according to the invention is applied on the aerial parts of plants.

The fungi which are phytopathogenic towards crops which can be combatted by this process are in particular those:

from the Oomycetes group:
from the Phytophthora genus, such as *Phytophthora infestans* (downy mildew of the Solanaceae, in particular of potatoes or tomatoes), *Phytophthora citrophthora, Phytophthora capsici, Phytophthora cactorum, Phytophthora palmivora, Phytophthora cinnamoni, Phytophthora megasperma* or *Phytophthora parasitica*, from the Peronosporaceae family, in particular *Plasmopara viticola* (grape downy mildew), *Plasmopara halstedei* (sunflower downy mildew), Pseudoperonospora sp (in particular downy mildew of cucurbits and of hops), *Bremia lactucae* (lettuce downy mildew) or *Peronospora tabacinae* (tobacco downy mildew), from the Adelomycetes group:
from the Alternaria genus, for example *Alternaria solani* (alternaria disease of the Solanaceae and in particular of tomatoes and potatoes),
from the Guignardia genus, in particular *Guignardia bidwellii* (black rot of grapes),
from the Oidiums group, for example grape powdery mildew (*Uncinula necator*); powdery mildew of legumes, for example *Erysiphe polygoni* (powdery mildew of crucifers); *Leveillula taurica, Erysiphe cichoracearum, Sphaerotheca fuligena;* (powdery mildew of cucurbits, of composites or of tomatoes); *Erysiphe communis* (beet and cabbage powdery mildew); *Erysiphe pisi* (pea or lucerne powdery mildew); *Erysiphe polyphaga* (bean and cucumber powdery mildew); *Erysiphe umbelliferarum* (powdery mildew of the Umbelliferae, in particular of carrots); *Sphaerotheca humuli* (hop powdery mildew); or *Erysiphe graminis* (powdery mildew of cereals),
from the Septoria genus, for example *Septoria nodorum* or *Septoria tritici* (septoria disease of cereals);
from the Basidiomycetes group:
from the Puccinia genus, for example *Puccinia recondita* or *striiformis* (wheat rusts).

A classification made no longer by targeted fungi but by target crops can be illustrated as below:

grapes: powdery mildew (Uncinula necator), downy mildew (*Plasmopara viticola*), excoriosis (*Phomopsis viticola*) and black rot (*Guignardia bidwellii*), Solanaceae: downy mildew (*Phytophthora infestans*), alternaria disease (Alternaria solani) and rot (*Botrytis cinerea*), vegetable crops: downy mildews (Peronospora sp., *Bremia lactucae,* Pseudoperonospora sp. or alternaria disease (Alternaria sp.), sclerotinia disease (Sclerotinia sp.), rot (*Botrytis cinerea*) or powdery mildew (Erysiphe sp. or *Sphaerotheca fuliginea*), arboriculture: scab (*Venturia inaequalis*), powdery mildew (*Podosphaera leucotricha*) and monilia disease (*Monilia fructigena*), citrus fruits: scab (*Elsinoe fawcetti*), melanose (*Phomopsis citri*) and diseases due to Phytophthora sp., bananas: cercospora disease (*Mycosphaerella figiensis*), lawns: rust, powdery mildew, helminthosporium disease or soil diseases (*Microdochium nivale,* Pythium sp., *Rhizoctonia solani,* and the like).

The fungicidal combination which is the subject of the invention in applied by means of various treatment processes, such as:

spraying the liquid comprising the said composition on the aerial parts of the crops to be treated, dusting, the incorporation of granules or of powders into the soil, sprinkling, injecting into trees or painting.

The spraying of a liquid on the aerial parts of the crops to be treated is the preferred treatment process.

"Effective and non-phytotoxic amount" is understood to mean an amount of composition according to the invention which is sufficient to make possible control or destruction of the fungi present or capable of appearing on the crops and which does not result in any substantial phytotoxicity symptoms respect to the said crops. Such an amount is capable of varying within wide limits depending on the fungi to be controlled, the type of crop, the weather conditions and the compounds included in the fungicidal composition according to the invention. This amount can be determined by systematic tests in the field, within the scope of the person skilled in the art.

The use doses during the implementation of the process according to the invention will then generally be:

on grapes, vegetable crops, Solanaceae, bananas, arboriculture or citrus fruits:

500 to 5000 g of compound B, eg fosetyl-Al+50 to 500 g/ha of compound A and more precisely 1000 to 3000 g+100 to 400 g/ha, i.e. a total dose of composition according to the invention of from 550 to 5500 g/ha, preferably from 1100 to 3400 g/ha, on lawns:

5000 to 25000 g of compound B eg fosetyl-Al+100 to 2000 g/ha of compound A and more precisely 10000 to 20000 g+250 to 1000 g/ha, i.e. a total dose of composition according to the invention of from 5100 to 27000 g/ha, preferably from 10250 to 21000 g/ha.

The following examples are given purely by way of illustration of the invention, which they do not limit in any way.

In the figures appended to the present text, the dose of each active material, taken in isolation, required for control of the phytopathogenic fungus at the level indicated is compared with that of the 2 active materials taken as a mixture. The effective dose of each active material taken in isolation is shown on the axis of the abscissae and of the ordinates and a straight line is traced cutting these 2 axes and connecting these 2 doses. When an active material taken in isolation in not effective, the straight line is parallel to the axis of the coordinates which shows the doses of this active material. As regards the 2 active materials taken as a mixture, the dose of the mixture at a given ratio in shown by a point.

EXAMPLE 1

In vivo Test of the Combination of ICIA5504 with Fosetyl-Al with Respect to *Plasmopara viticola* (Grape Downy Mildew) by Preventive Treatment 72 Hours Before Infection A suspension comprising the compounds A and B in a liquid mixture composed of a surface-active agent (oleate of polyoxyethylenated derivative of sorbitan) and water is prepared.

The component B is fosetyl-Al; the A/B ratio is 0.05, 0.07 and 0.1 (B/A=20, 15 and 10).

Vine (*Vitis vinifera*) cuttings, variety Chardonnay, are grown in small pots. When these seedlings are 2 months old (8- to 10-leaf stage, height of 10 to 15 cm), they are treated by spraying with the above suspension.

Seedlings, used an controls, are treated with a similar suspension but which does not contain active material ("formulation blank").

After 72 hours, each seedling is infected by spraying with an aqueous suspension of spores of *Plasmopara viticola*, which suspension is obtained from sporulated leaves infected 7 days previously. These spores are suspended at a concentration of 100,000 units per $cm^3$ of inoculum. Infection is carried out by spraying the inoculum at the undersurface of the leaves.

The infected seedlings are then incubated for seven days at 20–22° C. at 90–100% relative humidity under natural light.

Reading is carried out 7 days after infection, in comparison with the control seedlings.

The results obtained are reported in the form of points, corresponding to 50% destruction of the parasite, and are plotted on a Tammes isobole diagram which contains, on the abscissa, the doses of A expressed in ppm (mg/l) and, on the ordinate, the doses of B, also in ppm (mg/l).

The diagram of FIG. 1 is obtained. It appears that the addition of fosetyl-Al makes it possible, in an entirely unexpected way, to lower the dose of A necessary for the destruction of 50% of the parasite below 1.5 ppm (mg/l), which corresponds to the dose of A alone which it is necessary to apply to obtain the same percentage of destruction.

The arrangement of the points obtained therefore shows an effect described, according to the Tammes method mentioned above, as a "two-sided effect". This arrangement corresponds to a type-III isobole according to the said method (page 75 of the corresponding bibliographical reference already cited) and is characteristic of a synergy.

EXAMPLE 2

In vivo Test of the Combination of SSF-129 with Fosetyl-Al with Respect to *Plasmopara viticola* (Grape Downy Mildew) by Preventive Treatment 72 Hours Before Infection The same procedure is carried out as in EXAMPLE 1 but replacing the compound A (ICIA5504) by SSF-129.

The component B is still fosetyl-Al; the A/B ratio is 0.07, 0.1 and 0.2 (B/A=5, 10 and 15).

Figure 2:
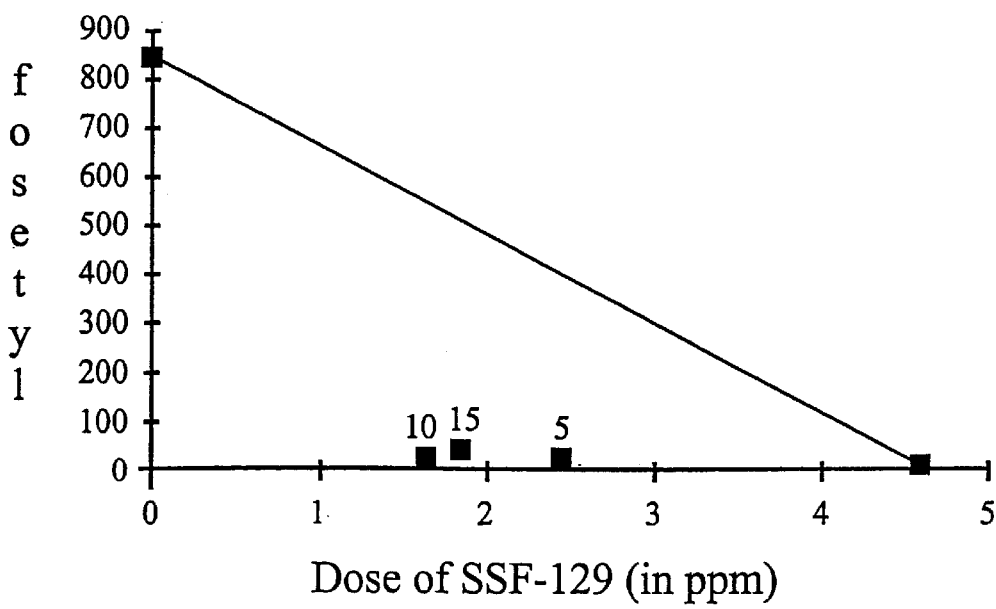
FIG. 2 is an isobole plot for SSF-129, i.e. N-methyl-(E)-methoxyimino[2-(2,5-dimethylphenoxymethyl)phenyl]acetamide, and fosetyl-Al in Chardonnay vine cuttings against *Plasmopara viticola*.

The diagram of FIG. 2 is obtained. It appears that the addition of fosetyl-Al makes it possible, in an entirely unexpected way, to lower the dose of A necessary for the destruction of 50% of the parasite below 4.6 pmm (mg/l), which corresponds to the dose of A alone which it is necessary to apply to obtain the same percentage of destruction.

The arrangement of the points obtained therefore shows an effect described, according to the Tammes method mentioned above, as a "two-sided effect". This arrangement corresponds to a type-III isobole according to the said method (page 75 of the corresponding bibliographical reference already cited) and is characteristic of a synergy.

What is claimed is:

1. A fungicidal composition comprising a synergistic fungicidally effective amount of a compound A which is methyl (E)-methoxyimino[α-(o-tolyloxy)-o-tolyl]acetate and a compound B which is phosphorous acid, a metal phosphite or an alkali metal or alkaline-earth metal salt of phosphorous acid, the A/B ratio by weight being from 0.004 to 1.

2. A fungicidal composition according to claim 1, wherein the A/B ratio by weight is from 0.0125 to 0.4.

3. A process for the curative or preventative control of phytopathogenic fungi in plants, said process comprising applying to plants or to the locus in which they grow a synergistic fungicidally effective non-phytotoxic amount of a compound A which is methyl (E)-methoxyimino[α-(o- tolyloxy)-o-tolyl]acetate and a compound B which is phosphorous acid, a metal phosphite or an alkali metal or alkaline-earth metal salt of phosphorous acid, the A/B ratio by weight being from 0.004 to 1.

4. A process according to claim 3, wherein the A/B ratio by weight is from 0.0125 to 0.4.

5. A fungicidal composition comprising a synergistic fungicidally effective amount of a compound A which is methyl (E)-methoxyimino[α-(o-tolyloxy)-o-tolyl]acetate and a compound B which is fosetyl-Al, the A/B ratio by weight being from 0.004 up to but not including 0.4.

6. A fungicidal composition according to claim 5, wherein the A/B ratio by weight is from 0.0125 up to but not including 0.4.

7. A fungicidal composition according to claim 5, wherein the A/B ratio by weight is from 0.01 up to but not including 0.4.

8. A fungicidal composition according to claim 5, wherein the A/B ratio by weight is from 0.033 up to but not including 0.4.

9. A fungicidal composition according to claim 5, wherein the A/B ratio by weight is from 0.004 up to but not including 0.4.

10. A fungicidal composition according to claim 5, wherein the A/B ratio by weight is from 0.0125 to 0.1.

11. A fungicidal composition according to claim 5, further comprising at least one member selected from the group consisting of an agriculturally acceptable solid or liquid vehicle and an agriculturally acceptable surface-active agent.

12. A fungicidal composition according to claim 11, comprising from 0.05% to 95% by weight of compounds A and B.

13. A process for the curative or preventative control of phytopathogenic fungi in plants, said process comprising applying to plants or to the locus in which they grow a synergistic fungicidally effective non-phytotoxic amount of a compound A which is methyl (E)-methoxyimino[α-(o-tolyloxy)-o-tolyl]acetate and a compound B which is fosetyl-Al, the A/B ratio by weight being from 0.004 up to but not including 0.4.

14. A process according to claim 13, wherein the A/B ratio by weight is from 0.0125 up to but not including 0.4.

15. A process according to claim 13, wherein the synergistic fungicidally effective non-phytotoxic amount of A and B is applied to crops or lawns to control fungi which are phytopathogenic towards crops or lawns, respectively.

16. A process according to claim 15, wherein the synergistic fungicidally effective non-phytotoxic amount of A and B is applied to the aerial parts of the plants.

17. A process according to claim 15, wherein the synergistic fungicidally effective non-phytotoxic amount of A and B is applied to crops and wherein the A/B ratio by weight is from 0.01 up to but not including 0.4.

18. A process according to claim 15, wherein the synergistic fungicidally effective non-phytotoxic amount of A and B is applied to crops and wherein the A/B ratio by weight is from 0.033 up to but not including 0.4.

19. A process according to claim 15, wherein the synergistic fungicidally effective non-phytotoxic amount of A and B is applied to crops at a dose rate of from 550 to 5500 g/ha.

20. A process according to claim 15, wherein the synergistic fungicidally effective non-phytotoxic amount of A and B is applied to crops at a dose rate of from 1100 to 3400 g/ha.

21. A process according to claim 17, wherein the synergistic fungicidally effective non-phytotoxic amount of A and B is applied at a dose rate of from 550 to 5500 g/ha.

22. A process according to claim 17, wherein the synergistic fungicidally effective non-phytotoxic amount of A and B is applied at a dose rate of from 1100 to 3400 g/ha.

23. A process according to claim 18, wherein the synergistic fungicidally effective non-phytotoxic amount of A and B is applied at a dose rate of from 550 to 5500 g/ha.

24. A process according to claim 18, wherein the synergistic fungicidally effective non-phytotoxic amount of A and B is applied at a dose rate of from 1100 to 3400 g/ha.

25. A process according to claim 15, wherein the synergistic fungicidally effective non-phytotoxic amount of A and B is applied to lawns and wherein the A/B ratio by weight is from 0.004 up to but not including 0.4.

26. A process according to claim 15, wherein the synergistic fungicidally effective non-phytotoxic amount of A and B is applied to lawns and wherein the A/B ratio by weight is from 0.0125 to 0.1.

27. A process according to claim 15, wherein the synergistic fungicidally effective non-phytotoxic amount of A and B is applied to lawns at a dose rate of from 5100 to 27000 g/ha.

28. A process according to claim 15, wherein the synergistic fungicidally effective non-phytotoxic amount of A and B is applied to lawns at a dose rate of from 10250 to 21000 g/ha.

29. A process according to claim 25, wherein the synergistic fungicidally effective non-phytotoxic amount of A and B is applied to lawns at a dose rate of from 5100 to 27000 g/ha.

30. A process according to claim 25, wherein the synergistic fungicidally effective non-phytotoxic amount of A and B is applied to lawns at a dose rate of from 10250 to 21000 g/ha.

31. A process according to claim 26, wherein the synergistic fungicidally effective non-phytotoxic amount of A and B is applied to lawns at a dose rate of from 5100 to 27000 g/ha.

32. A process according to claim 26, wherein the synergistic fungicidally effective non-phytotoxic amount of A and B is applied to lawns at a dose rate of from 10250 to 21000 g/ha.

33. A fungicidal composition comprising a synergistic fungicidally effective amount of a compound A which is methyl (E)-methoxyimino[α-(o-tolyloxy)-o-tolyl]acetate and a compound B which is phosphorous acid, a metal phosphite or an alkali metal or alkaline-earth metal salt of phosphorous acid, the A/B ratio by weight being from 0.1 to 0.4.

34. A fungicidal composition according to claim 33, wherein the A/B ratio by weight is 0.1.

35. A process for the curative or preventative control of phytopathogenic fungi in plants, said process comprising applying to plants or to the locus in which they grow a synergistic fungicidally effective non-phytotoxic amount of a compound A which is methyl (E)-methoxyimino[α-(o-tolyloxy)-o-tolyl]acetate and a compound B which is phosphorous acid, a metal phosphite or an alkali metal or alkaline-earth metal salt of phosphorous acid, the A/B ratio by weight being from 0.1 to 0.4.

36. A process according to claim 35, wherein the A/B ratio by weight is 0.1.

37. A process according to claim 35, wherein the synergistic fungicidally effective non-phytotoxic amount of A and B is applied to crops or lawns to control fungi which are phytopathogenic towards crops or lawns, respectively.

38. A process according to claim 37, wherein the synergistic fungicidally effective non-phytotoxic amount of A and B is applied to crops at a dose rate of from 550 to 5500 g/ha, the dose rate of A falling within the range of from 50 to 500 g/ha and the dose rate of B falling within the range of from 500 to 5000 g/ha.

39. A process according to claim 37, wherein the synergistic fungicidally effective non-phytotoxic amount of A and B is applied to crops at a dose rate of from 1100 to 3400 g/ha, the dose rate of A falling within the range of from 100 to 400 g/ha and the dose rate of B falling within the range of from 1000 to 3000 g/ha.

40. A process according to claim 37, wherein the synergistic fungicidally effective non-phytotoxic amount of A and B is applied to lawns at a dose rate of from 5100 to 27000 g/ha, the dose rate of A falling within the range of from 100 to 2000 g/ha and the dose rate of B falling within the range of from 5000 to 25000 g/ha.

41. A process according to claim 37, wherein the synergistic fungicidally effective non-phytotoxic amount of A and B is applied to lawns at a dose rate of from 10250 to 21000 g/ha, the dose rate of A falling within the range of from 250 to 1000 g/ha and the dose rate of B falling within the range of from 10000 to 20000 g/ha.

42. A fungicidal composition comprising a synergistic fungicidally effective amount of a compound A which is methyl (E)-methoxyimino[α-(o-tolyloxy)-o-tolyl]acetate and a compound B which is fosetyl-Al, the A/B ratio by weight being from 0.1 up to but not including 0.4.

43. A fungicidal composition according to claim 42, wherein the A/B ratio by weight is 0.1.

44. A fungicidal composition according to claim 42, further comprising at least one member selected from the group consisting of an agriculturally acceptable solid or liquid vehicle and an agriculturally acceptable surface-active agent.

45. A fungicidal composition according to claim 44, comprising from 0.05% to 95% by weight of compounds A and B.

46. A process for the curative or preventative control of phytopathogenic fungi in plants, said process comprising applying to plants or to the locus in which they grow a synergistic fungicidally effective non-phytotoxic amount of a compound A which is methyl (E)-methoxyimino[α-(o-tolyloxy)-o-tolyl]acetate and a compound B which is fosetyl-Al, the A/B ratio by weight being from 0.1 up to but not including 0.4.

47. A process according to claim 46, wherein the A/B ratio by weight is 0.1.

48. A process according to claim 46, wherein the synergistic fungicidally effective non-phytotoxic amount of A and B is applied to crops or lawns to control fungi which are phytopathogenic towards crops or lawns, respectively.

49. A process according to claim 48, wherein the synergistic fungicidally effective non-phytotoxic amount of A and B is applied to the aerial parts of the plants.

50. A process according to claim 48, wherein the synergistic fungicidally effective non-phytotoxic amount of A and B is applied to crops at a dose rate of from 550 to 5500 g/ha.

51. A process according to claim 48, wherein the synergistic fungicidally effective non-phytotoxic amount of A and B is applied to crops at a dose rate of from 1100 to 3400 g/ha.

52. A process according to claim 48, wherein the synergistic fungicidally effective non-phytotoxic amount of A and B is applied to lawns at a dose rate of from 5100 to 27000 g/ha.

53. A process according to claim 48, wherein the synergistic fungicidally effective non-phytotoxic amount of A and B is applied to lawns at a dose rate of from 10250 to 21000 g/ha.

* * * * *